(12) United States Patent
Senetar et al.

(10) Patent No.: US 11,577,237 B2
(45) Date of Patent: Feb. 14, 2023

(54) PROCESS AND APPARATUS FOR REGENERATING CATALYST WITH SUPPLEMENTAL FUEL

(71) Applicant: UOP LLC, Des Plaines, IL (US)

(72) Inventors: John J. Senetar, Naperville, IL (US); Lev Davydov, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 480 days.

(21) Appl. No.: 16/714,383

(22) Filed: Dec. 13, 2019

(65) Prior Publication Data
US 2021/0178382 A1   Jun. 17, 2021

(51) Int. Cl.
*B01J 8/18* (2006.01)
*B01J 38/30* (2006.01)
*C07C 5/32* (2006.01)

(52) U.S. Cl.
CPC ............. *B01J 38/30* (2013.01); *B01J 8/1827* (2013.01); *B01J 8/1863* (2013.01); *C07C 5/321* (2013.01)

(58) Field of Classification Search
CPC ........ B01J 38/30; B01J 8/1827; B01J 8/1863; B01J 29/90; B01J 38/02; B01J 8/28; C07C 5/321
USPC ......................................................... 502/41
See application file for complete search history.

(56) References Cited

U.S. PATENT DOCUMENTS

| 5,143,875 | A | * | 9/1992 | Owen | ...................... B01J 38/36 502/40 |
| 5,979,799 | A | † | 11/1999 | Chen | |
| 6,558,531 | B2 | | 5/2003 | Steffens | |
| 7,026,262 | B1 | * | 4/2006 | Palmas | ................... F27B 15/00 502/41 |
| 8,293,670 | B2 | † | 10/2012 | Myers | |
| 8,513,149 | B2 | † | 8/2013 | Myers | |
| 8,753,502 | B1 | | 6/2014 | Sexton | |

(Continued)

FOREIGN PATENT DOCUMENTS

| FR | 2476672 A1 | 8/1981 |
| WO | 2011071584 A2 | 6/2011 |
| WO | 2016036852 A1 | 3/2016 |

OTHER PUBLICATIONS

PCT Search Report and Written Opinion dated Mar. 11, 2020.
Bejcek, "Bubble Size Above an Isolated Gas Jet Penetrating a Fluidized Bed", Feb. 27, 1987.
Simmie, "Detailed Chemical Kinetic Models for the Combustion of Hydrocarbon Fuels".

(Continued)

*Primary Examiner* — Huy Tram Nguyen
(74) *Attorney, Agent, or Firm* — Paschall & Associates, LLC; James C. Paschall

(57) ABSTRACT

Higher temperature regenerated dehydrogenation catalyst is mixed with the lower temperature spent dehydrogenation catalyst from a dehydrogenation reaction to heat the spent catalyst. Air or other oxygen containing gas may be introduced to facilitate mixing. The mixing of hot regenerated catalyst with cooler spent catalyst increases the temperature of the spent catalyst and makes the coke on catalyst and in the supplemental fuel gas instantly ready to combust without the delay necessary to heat up the spent catalyst to combustion temperature. The regenerated dehydrogenation catalyst may be mixed with the spent dehydrogenation catalyst before the mixture of catalyst is contacted with the supplemental fuel gas. Combustion with fuel gas should be conditioned to avoid generation of a flame.

25 Claims, 3 Drawing Sheets

(56) References Cited

U.S. PATENT DOCUMENTS

| | | | |
|---|---|---|---|
| 8,871,151 B2 * | 10/2014 | Davydov | B01J 8/1845 |
| | | | 422/144 |
| 9,266,103 B1 * | 2/2016 | Davydov | B01J 8/1827 |
| 9,597,652 B1 | 3/2017 | Pretz | |
| 9,889,418 B2 * | 2/2018 | Pretz | B01J 8/1827 |
| 10,227,271 B2 | 3/2019 | Pretz | |
| 10,343,128 B2 † | 7/2019 | Li | |
| 2009/0264279 A1 * | 10/2009 | Hedrick | B01J 38/02 |
| | | | 422/144 |
| 2016/0199823 A1 * | 7/2016 | Nawaz | C07C 5/3337 |
| | | | 502/73 |
| 2019/0225563 A1 † | 6/2019 | Pretz | |

OTHER PUBLICATIONS

Berkeley, "GRI-Mech Project Overview", Dec. 12, 2019.
Sotudeh-Gharebagh, "The Heterogeneous and Homogeneous Combustion of Methane over Inert Particles", Jul. 21, 2003.
Yang, Handbook of Fluidization and Fluid-Particle Systems, Chapter 3., 2003, Marcel, Dekker, Inc., New York.†
Li et. al.: Numerical Simulation of Influence of Feed Injection on Hydrodybamic Behavior and Catalytic Cracking Reactions in a Fcc Riser Under Reactive Conditions, pp. 11084-11098., vol. 50, 2013, Jul. 18, 2013, ACS Publications, Industrial & Engineering Chemistry Research.†

\* cited by examiner
† cited by third party

PROCESS AND APPARATUS FOR REGENERATING CATALYST WITH SUPPLEMENTAL FUEL

FIELD

The field is the regeneration of catalyst and particularly the combustion of coke from fluidized catalyst.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion. Fluid catalytic cracking (FCC) is another endothermic process which produces substantial ethylene and propylene.

In PDH and FCC reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. However, the coke produced in the PDH reaction can provide insufficient heat from combustion in the regenerator to promote the endothermic dehydrogenation process. Insufficient heat from regenerated catalyst delivered to the reactor has been observed recently in FCC due to advances in stripping efficiency resulting in less hydrocarbons on spent catalyst transported to the catalyst regenerator. Hence, supplemental fuel such as fuel gas may be fed to the catalyst regenerator to heat the catalyst sufficiently to transfer sufficient enthalpy to drive the endothermic reaction. Conversely, if insufficient heat is provided to drive the endothermic reaction, olefin production can suffer.

Dehydrogenation catalyst may incorporate a dehydrogenation metal with a molecular sieve or an amorphous material. The catalyst must be sufficiently robust and appropriately sized to be able to resist the attrition expected in a fluidized system. FCC catalyst is typically a Y zeolite with an optional MFI zeolite to boost propylene production.

The regeneration process and equipment must be designed to minimize damage to the catalyst and to the regeneration equipment. This can be particularly challenging when fuel gas is added to the regenerator which can promote hot spots in areas where fuel gas combusts with insufficient means to disperse the heat. A high degree of vapor and catalyst mixing ensures complete combustion of the supplemental fuel gas and good heat transfer between vapor and catalyst. The catalyst is a large heat sink, so the supplemental fuel gas should be burned while in intimate contact with the dense catalyst phase to avoid excessively high dilute catalyst phase temperature. The catalyst density in the dense catalyst phase is at least 200 kg/m$^3$ (12.5 lb/ft), and the catalyst density in the dilute catalyst phase is no more than 100 kg/m$^3$ (6.3 lb/ft). Excess dilute catalyst phase temperatures can result in thermal damage to the surrounding catalyst and regeneration equipment because the heat is insufficiently dispersed in the absence of the dense catalyst phase.

Poor mixing between air and the supplemental fuel gas or insufficient contact time between fuel gas, air and catalyst may result in incomplete combustion of the coke on the catalyst or the fuel gas. Un-combusted fuel gas that persists downstream of primary catalyst separation equipment will tend to burn in the dilute catalyst phase resulting in excessively high temperature because most of the catalyst heat sink has already been separated from the gases in a phenomenon known as afterburn. If for some reason the unburned fuel gas exits the regenerator without completely combusting, the vapor exiting the regenerator has the possibility of burning in downstream equipment which is not rated for the high temperatures common in a regenerator or result in unburned fuel gas being released to the atmosphere. Conditions in the regenerator should be selected to minimize flame development which can damage catalyst and equipment due to its intense heat.

In conventional fluidized dehydrogenation catalyst regenerators spent catalyst is heated by the heat of combustion of the coke and supplemental fuel gas. Spent catalyst entering the regenerator is cooler and reduces the temperature of the regenerator. Supplemental fuel gas and coke on catalyst may need to be heated to combustion temperature before they can combust in the regenerator.

There is a need, therefore, for improved methods of contacting dehydrogenation catalyst with fuel gas and air in a catalyst regeneration process.

BRIEF SUMMARY

Higher temperature regenerated catalyst is mixed with the lower temperature spent catalyst to heat the spent catalyst. Air or other oxygen supply gas may be introduced to facilitate mixing. The mixing of hot regenerated catalyst with cooler spent catalyst increases the catalyst density in the regenerator and provides sufficient catalyst to absorb heat without excess temperature rise thereby protecting catalyst and equipment. The temperature of the spent catalyst is also increased making the coke on catalyst and the supplemental fuel gas instantly ready to combust without the delay necessary to heat up the spent catalyst to combustion temperature. The regenerated catalyst may be mixed with the spent catalyst before the mixture of catalyst is contacted with the supplemental fuel gas. The fuel gas may be distributed under conditions that provide a particle Reynolds No. of between about 50 and about 4000 to assure steady combustion.

DEFINITIONS

Figure 1:
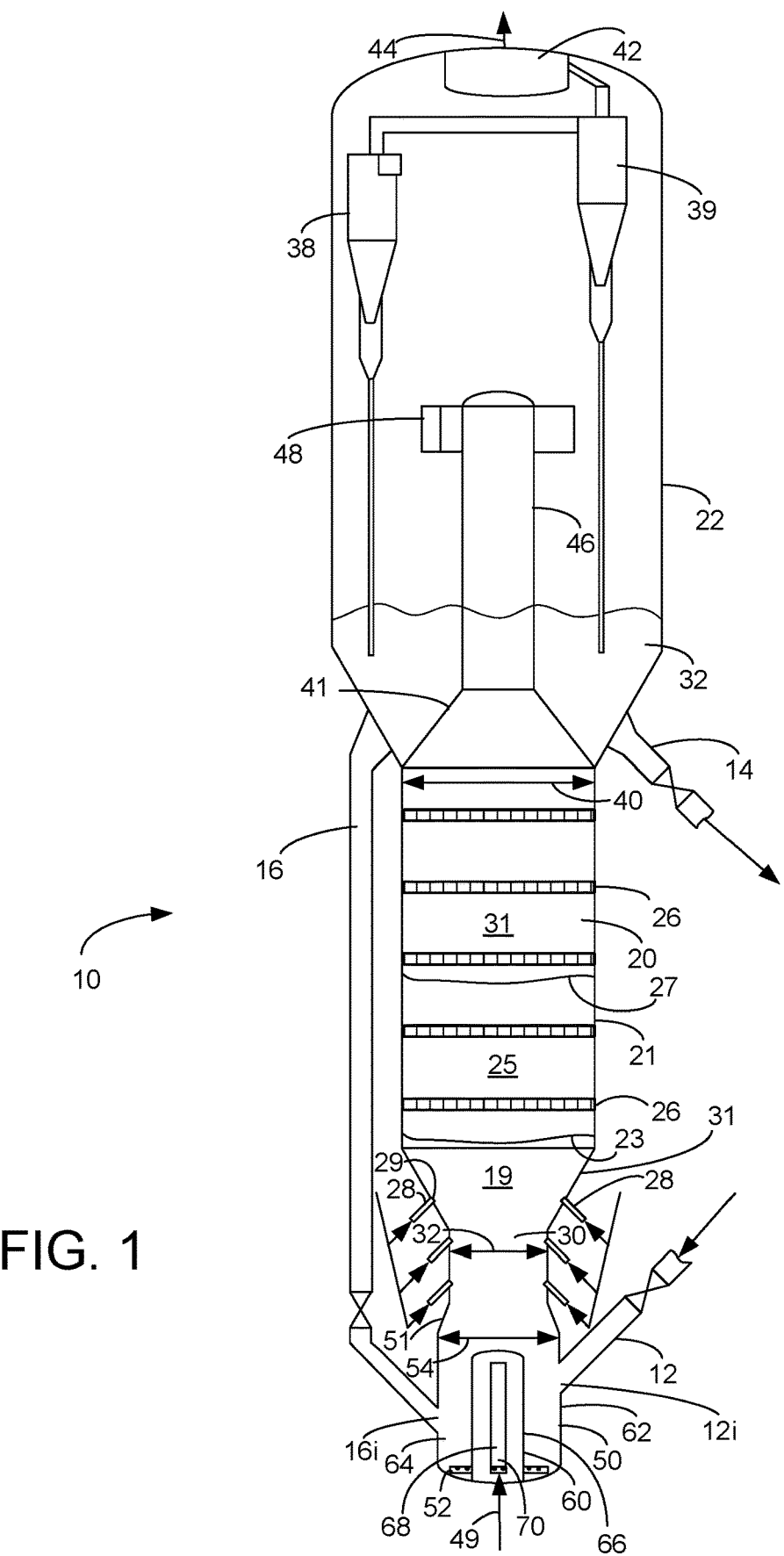
FIG. 1 is a schematic drawing of a process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

The term "fuel gas" comprises hydrocarbons, hydrogen and mixtures thereof.

As used herein, the term "predominant" or "predominate" means greater than 50%, suitably greater than 75% and preferably greater than 90%.

DETAILED DESCRIPTION

The disclosure provides a process and apparatus that promotes thorough contacting between gas and catalyst with supplemental fuel combustion to decarbonize and heat the catalyst to temperatures sufficient to drive the endothermic reactions when the regenerated catalyst is transferred to the reactor. Recycle of the regenerated catalyst provides sufficient heat sink in the regenerator to avoid excess temperature rise which could damage catalyst and equipment. The supplemental fuel gas can be contacted with catalyst at a higher temperature than the lower temperature spent catalyst. The higher temperature catalyst makes the coke on spent catalyst and the supplemental fuel gas more ready to combust without the delay necessary to heat up the spent catalyst to combustion temperature.

Mixing the spent catalyst and at least partially regenerated catalyst or injecting the fuel gas into the regenerated catalyst can enable distribution of supplemental fuel gas to the catalyst at a temperature of at least 660° C. No catalyst residence time need be wasted in the regenerator to heat the spent catalyst to combustion temperature. Oxygen supply gas may be used to fluidize the mixture of spent catalyst and regenerated catalyst and to also lift the catalyst in the regenerator. The oxygen supply gas, which may be air, contains oxygen which is necessary for combustion. Recycling regenerated catalyst to the regenerator maximizes the contact time in which combustion gases, oxygen and fuel gas, are in the presence of the dense catalyst phase which can better absorb the heat without excess temperature rise. Regenerated catalyst recycling also provides an ability to vary the ratio of mass flow rates of spent catalyst and recycled regenerated catalyst without affecting the flow rate of regenerated catalyst to the reactor.

The teachings herein may be applicable to any process that requires catalyst to be regenerated for an endothermic reaction. Paraffin dehydrogenation (PDH) and fluid catalytic cracking (FCC) are examples of such processes. FCC catalyst is used to crack larger hydrocarbon molecules to smaller hydrocarbon molecules at around atmospheric pressure and about 427° C. (800° F.) to 538° C. (1000° F.) and a catalyst to oil ratio of about 5 to about 30. PDH catalyst is used in a dehydrogenation reaction process to catalyze the dehydrogenation of ethane and/or propane to ethylene and propylene. The PDH process will be described exemplarily to illustrate the disclosed apparatus and process.

The conditions in the dehydrogenation reaction may include a temperature of about 500 to about 800° C., a pressure of about 40 to about 310 kPa and a catalyst to oil ratio of about 5 to about 100. The dehydrogenation reaction may be conducted in a fluidized manner such that gas, which may be the reactant paraffins or a fluidizing inert gas, is distributed to the reactor in a way that lifts the dehydrogenation catalyst in the reactor vessel while catalyzing the dehydrogenation of propane and/or ethane. During the catalytic dehydrogenation reaction, coke is deposited on the dehydrogenation catalyst so as to reduce the activity of the catalyst. The dehydrogenation catalyst must then be regenerated.

A spent catalyst standpipe 12 transports spent catalyst from the dehydrogenation reactor to the catalyst regenerator 10 through a control valve. Heated regenerated catalyst from the regenerator 10 is transported back to the dehydrogenation reactor in a return regenerated catalyst standpipe 14 through a control valve with less concentration of carbon or coke on catalyst than in the spent catalyst standpipe 12 to catalyze the dehydrogenation reaction and to provide sufficient enthalpy to drive the endothermic dehydrogenation reaction.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The primary active component ranges from about 10 to about 50 weight percent of the catalyst and may have a lattice structure that limits the size range of hydrocarbon molecules that can enter the lattice. The molecular sieves appropriate for the primary active component should have medium and smaller average pore size. Typically, molecular sieves with medium and smaller average pore size have pores with openings of no more than 0.7 nm in effective diameter defined by rings of ten or fewer.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may be also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, it is preferred to use about 0.05 to about 2 wt % noble metal.

The spent catalyst is transported to the catalyst regenerator 10 to combust the coke and regenerate the spent catalyst into regenerated catalyst. The catalyst regenerator 10 includes a combustion chamber 20 and a catalyst separator 22 in which the regenerated catalyst is separated from flue gas generated in the combustion chamber 20. An oxygen supply gas distributor 52 provides oxygen supply gas from an oxygen supply gas line 49 to the combustion chamber 20 which lifts the spent catalyst in the combustion chamber 20 into the separation chamber 22. The coke is burned off the spent catalyst by contact with the oxygen supply gas at regeneration conditions. In an exemplary embodiment, air is used as the oxygen supply gas, because air is readily available and provides sufficient oxygen for combustion, but other gases with a sufficient concentration of oxygen could also be used, such as purified oxygen. If air is used as the oxygen supply gas, about 10 to about 15 kg of air is required per kg of coke burned off of the spent catalyst. Exemplary regeneration conditions include a temperature from about 500° C. (900° F.) to about 900° C. (1700° F.) and a pressure of about 150 kPa (gauge) (20 psig) to about 450 kPa (gauge) (70 psig) in the regenerator 10.

Catalyst, fuel gas and oxygen supply gas ascend in the combustion chamber 20 while coke is combusted from the catalyst and the fuel gas is also combusted to regenerate the catalyst and generate flue gas. Combustion gas and catalyst ascend in a fast-fluidized flow regime in which catalyst may slip relative to the gas and the gas can take indirect upward trajectories. The superficial velocity of the combustion gases in the combustion chamber is typically about 0.9 m/s (3 ft/s), preferably about 1.1 m/s (3.5 ft/s), to about 2.1 m/s (7 ft/s) to provide a fast-fluidized flow regime.

The combustion chamber 20 has a combustion chamber diameter indicated by the double headed arrow 40, where the combustion chamber diameter 40 is measured at the widest point of the combustion chamber 20 across a tubular wall 21 of the combustion chamber 20 which may be cylindrical. One or more gratings 26 may be installed across the cross section of the combustion chamber 20 to ensure proper flow and contacting, regulate bubble size and to prevent catalyst from bypassing oxygen and fuel gas contact. The gratings 26 may comprise a permeable barrier such as baffles or strips turned vertically on edge in a crisscross pattern.

The blend of gases and catalyst ascend from the combustion chamber 20 through a frustoconical transition section 41 into a riser 46 which has a smaller diameter than the diameter 40 of the combustion chamber 20. A blend of gases and catalyst accelerate in the narrower riser 46 and are discharged from a riser termination device 48 into the separation chamber 22. The riser termination device 48 utilizes horizontal, centripetal acceleration to separate regenerated catalyst from flue gas. The superficial gas velocity in the riser 46 will be about 6 m/s (20 ft/s) to about 15 m/s (50 ft/s) and constitute a dilute catalyst phase.

Regenerated catalyst separated from flue gas by the riser termination device 48 drops into a dense catalyst bed 32. The catalyst separation chamber 22 may include one or more regenerator cyclones 38 or other solid/gaseous separator devices to separate the regenerated catalyst still entrained in the flue gas. In an aspect, primary cyclones 38 may collect flue gas from the separation chamber 22 and transport the flue gas separated from catalyst to a secondary cyclone 39 to further separate regenerated catalyst from the flue gas before directing secondarily purified flue gas to the plenum 42. Flue gas is discharged from the regenerator 10 in a discharge line 44. Regenerated catalyst separated from flue gas in the cyclones 38, 39 is dispensed by dip legs into the dense bed 32. A return portion of the regenerated catalyst collected in the dense bed 32 of the catalyst separation chamber 22 is transported in the return regenerated catalyst standpipe 14 back to the dehydrogenation reactor for catalyzing dehydrogenation reactions. A recycle portion of the regenerated catalyst collected in the dense bed 32 of the catalyst separation chamber 22 is recycled in a recycle regenerated catalyst standpipe 16 back to the lower chamber 20 of the regenerator 10.

In an exemplary embodiment, the regenerator 10 includes a mixing chamber 50. The mixing chamber may be located at a lower end of the regenerator 10. The mixing chamber 50 may include a spent catalyst pipe inlet 12$i$ from the spent catalyst standpipe 12 which serves as an outlet for the spent catalyst standpipe. The mixing chamber 50 may also include a regenerated catalyst pipe inlet 16$i$ from the regenerated catalyst standpipe 16 which serves as an outlet for the regenerated catalyst standpipe. In an exemplary embodiment, the mixing chamber 50 has a mixing chamber diameter indicated by the double headed arrow 54. The mixing chamber diameter 54 is less than the combustion chamber diameter 40. The mixing chamber 50 may be cylindrical in some embodiments. The mixing chamber 50 is in downstream communication with the spent catalyst pipe inlet 12$i$ and the regenerated catalyst pipe inlet 16$i$. The spent catalyst pipe inlet 12$i$ discharges a stream of spent catalyst from a spent catalyst standpipe 12 into the mixing chamber 50, and the regenerated catalyst pipe inlet 16$i$ discharges the recycled portion of regenerated catalyst from the regenerated catalyst standpipe 16. The spent catalyst standpipe 12 may include a control valve thereon to control the rate of flow of the spent catalyst to the mixing chamber 50 from the dehydrogenation reactor. The recycle regenerated catalyst standpipe 16 may also include a control valve thereon to control the rate of flow of the regenerated catalyst recycled to the mixing chamber 50 from the separation chamber 22. In some embodiments, the catalyst is fluidized in the spent catalyst standpipe 12 and/or the recycle regenerated catalyst standpipe 16 to facilitate catalyst flow. One or both of the spent catalyst inlet 12$i$ and the regenerated catalyst inlet 16$i$ may optionally be tangentially connected to the mixing chamber 50 to impart an angular motion to the catalyst entering the mixing chamber 50 to promote mixing. Additionally, ramps (not illustrated) may be installed at the spent catalyst inlet 12$i$ and the regenerated catalyst inlet 16$i$ to further promote mixing. The ramps may direct the flowing catalyst upward, downward, or to one side or the other in various embodiments. An oxygen supply gas distributor 52 emits oxygen supply gas into the mixing chamber 50 to fluidize the catalyst within the mixing chamber 50 and lift the catalyst from the mixing chamber upwardly into the combustion chamber 20. The oxygen supply gas discharged from the oxygen supply distributor 52 includes oxygen necessary for combustion.

The mixing chamber 50 receives a stream of spent catalyst and a stream of regenerated catalyst and mixes them together to provide a mixture of catalyst. While mixing, the hotter regenerated catalyst heats the cooler spent catalyst which serves to provide a catalyst mixture at a temperature of at least 600° C., suitably at least 650° C. and preferably at least 660° C. Coke on catalyst or fuel gas in contact with the catalyst mixture will be inclined to combust with oxygen immediately at these temperatures. The mixing chamber 50 may have an inner diameter 54 that is smaller than an inner diameter 40 of the combustion chamber 20. The mixing chamber 50 may connect to the combustion chamber 20 through a mix transition 51 that may be frustoconical. The superficial gas velocity in the mixing chamber 50 may about 1.5 m/s (5 ft/s), to about 6 m/s (20 ft/s), and the catalyst density will be from about 240 kg/m³ (15 lb/ft³) to about 560 kg/m³ (35 lb/ft³) constituting a dense catalyst phase in the mixing chamber 50.

A dense catalyst bed 19 with catalyst in a dense catalyst phase will develop in the combustion chamber 20 such as below a transition phase 25 defined between a lower interphase 23 and an upper interphase 27. A dilute catalyst phase 31 will form above upper interphase 27 above the transition phase 25. The catalyst density in the dilute catalyst phase 31 above the upper interphase 27 will be from about 8 kg/m³ (0.5 lb/ft³) to about 80 kg/m³ (5 lb/ft³) in the dilute catalyst phase. The catalyst density in the dense catalyst bed 19 below the lower interphase 23 will be from about 320 kg/m³ (20 lb/ft³) to about 560 kg/m³ (35 lb/ft³). It is desired that most of the combustion of coke occur in the dense catalyst bed 19.

The rate of recycle of regenerated catalyst can be controlled by operation of the control valve on the recycle regenerated catalyst standpipe 16 independently of the rate of spent catalyst to the regenerator 10 by operation of the control valve on the spent catalyst pipe 12 to adjust the height of the dense catalyst phase and the dilute catalyst phase. Catalyst ascends through the dense catalyst phase in the dense catalyst bed 19 more slowly than through transition phase 25 and through the transition more slowly than through the dilute catalyst phase 31. The taller the dense catalyst bed 19 represented by the height of the lower interphase 23 the greater the residence time of catalyst in the regenerator 10 and particularly the residence time of the catalyst in the dense catalyst phase. Consequently, by adjusting the height of the lower interphase 23 through varying the recycle rate of regenerated catalyst through the control valve on the recycle regenerated catalyst standpipe 16, the residence time of catalyst in the regenerator 10 can be adjusted to ensure sufficient combustion and enthalpy absorbed by the catalyst and transferred to the dehydrogenation reactor. Moreover, the height of the lower interphase 23 can be adjusted to ensure that the combustion occurs in the dense catalyst bed 19 where sufficient volume of catalyst is present to absorb the heat of combustion without excess temperature rise.

The recycle rate of the regenerated catalyst through the recycle regenerated catalyst standpipe 16 to the mixing chamber 50 may be about 0.5 to about 10 times that of the rate of spent catalyst through the spent catalyst standpipe 12 to the mixing chamber. Suitably the recycle rate may be about 1 to about 5 times the rate of spent catalyst through the spent catalyst standpipe 12 to the mixing chamber 50

Oxygen supply gas such air, both oxygen supply gas and fuel gas, or an oxygen supply gas and fuel gas mixture may be fed from the oxygen supply gas line 49 to the oxygen supply gas distributor 52 in the mixing chamber 50. The distributor 52 distributes oxygen supply gas such as air to the catalyst entering the mixing chamber 50 to fluidize the catalyst in the mixing chamber to facilitate mixing and to lift the catalyst from the mixing chamber to the combustion chamber 20.

In some cases, coke on the spent catalyst may be insufficient to generate enough enthalpy from combustion to drive the endothermic reaction in the reactor. This can be the case with PDH. Hence, supplemental fuel gas is added to the regenerator to provide additional enthalpy to drive the endothermic reaction. The regenerator 10 may include a fuel distributor 28 for distributing fuel gas for combustion in the combustion chamber 20. In an embodiment, the fuel distributor may be located between the air distributor 52 and the lowest grating 26. The regenerator 10 may include a plurality of fuel distributors 28 for distributing fuel gas to the regenerator which may be located between the air distributor 52 and the lowest grating 26. A discharge nozzle 29 of the fuel distributors 28 may be located in the combustion chamber 20 or in the mixing chamber 50.

In an embodiment, the regenerator 10 may include a fuel distribution section 30 including one or more fuel distributors 28 comprising injectors that penetrate a wall 21 of the regenerator 10 and have only a single discharge nozzle 29 at an end of the fuel distributor 28. Each fuel distributor 28 may have the single discharge nozzle 29 that is proximate to the wall 21 of the regenerator. Fuel distributors 28 may be oriented to inject fuel gas inwardly and upwardly in the direction of catalyst flow and air flow. Discharge nozzles 29 of the fuel distributors 28 may be located in the fuel distribution section 30.

In the embodiment of FIG. 1, the fuel distribution section 30 may be located between the mixing chamber 50 and the combustion chamber 20 to inject fuel gas into the mixture of spent and regenerated catalyst and oxygen supply gas. In an aspect, the fuel distribution section 30 may have an inner diameter 32 that is smaller than an inner diameter 54 of the mixing chamber 50. The fuel distribution section 30 may have the frustoconical transition section 51 to graduate the increase of inner diameter between the fuel distribution section 30 and the mixing chamber 50. The fuel distribution section 30 may have an inner diameter 32 that is smaller than the inner diameter 40 of the combustion chamber 20. The combustion chamber 20 may connect to the fuel distribution section 30 through a mix transition 31 that may be frustoconical to graduate the increase of inner diameter between the fuel distribution section 30 and the combustion chamber 20. The inner diameter 32 of the fuel distribution section 30 is smaller than the inner diameter 54 of the mixing chamber 50 and the inner diameter 40 of the combustion chamber 20 to ensure that catalyst and gas can pass upwardly therethrough without significant hindrance from protruding fuel distributors, such as exhibited by chordal distributors, but still distribute fuel gas across the entire cross section of the fuel distribution section 30 for thorough distribution into the catalyst. The gas superficial velocity in the fuel distribution section 30 may be between about 3 m/s (10 ft/s) and 6 m/s (20 ft/s).

The fuel distributors 28 may be located in the frustoconical transition sections 31, 51 which may be considered part of the fuel distribution section 30. The fuel distribution section 30 may be considered part of the mixing chamber 50. By arranging the fuel distribution section 30 in this manner, fuel gas contacts the mixture of spent catalyst and regenerated catalyst exiting the mixing chamber 50.

Figure 2:
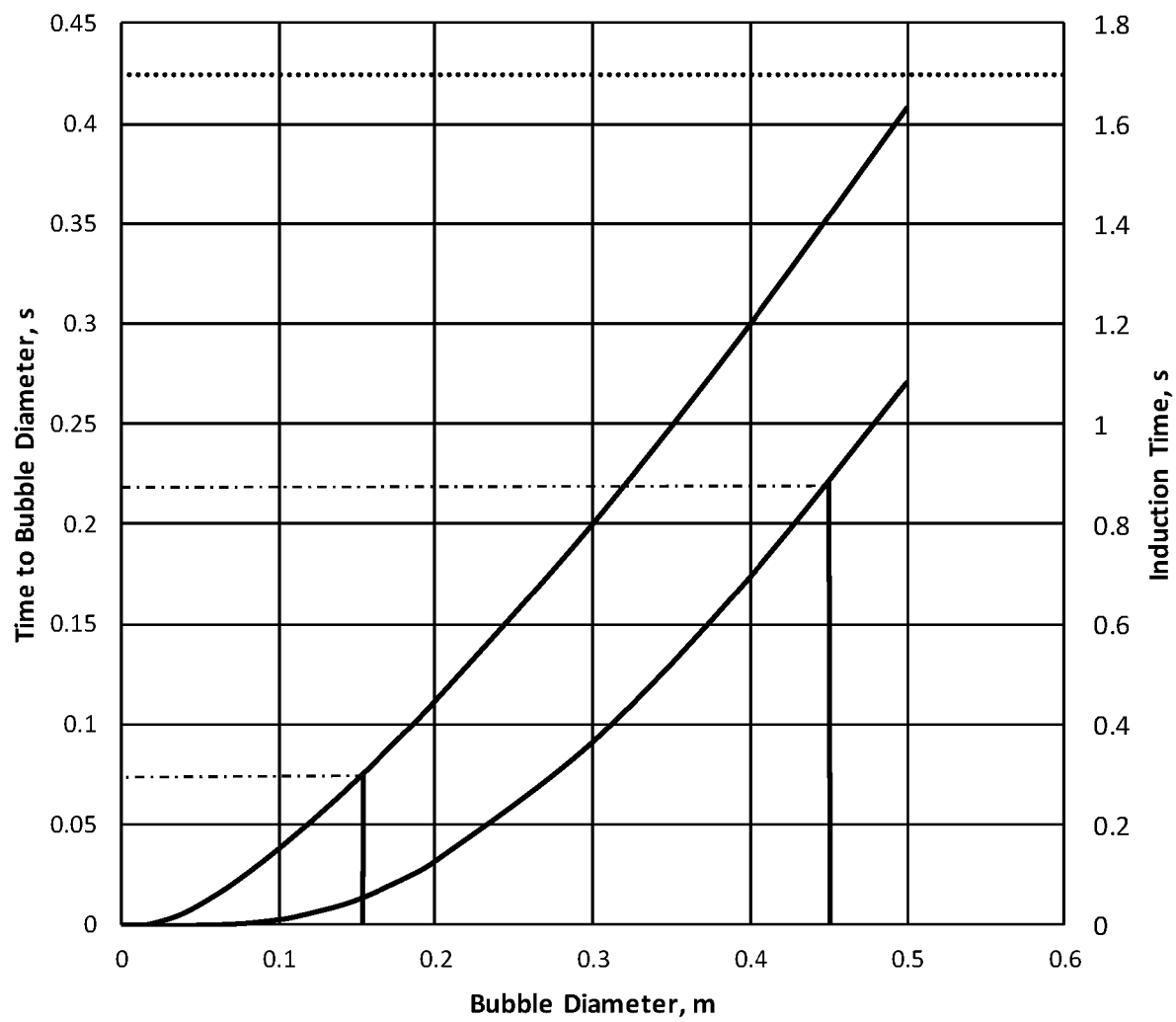
FIG. 2 is a plot of Time to Bubble Diameter and Induction Time vs. Bubble Diameter for a given Reynolds No.

FIG. 2 presents a plot of Time to Bubble Diameter and Induction Time vs. Bubble Diameter which follows a curve delineated by a particle Reynolds No. The left vertical axis is labeled with Time to Bubble Diameter, and the right vertical axis is labeled with Induction Time. The left vertical line in the plot represents the maximum stable bubble diameter at a particle Reynolds No. of 50, corresponding to the upper curve, for a fuel gas emitted from a jet of gas extending from the nozzle 29 of the fuel distributor 28. The jet is the stream of gas contiguous with the nozzle 29 of the fuel distributor 28. The dotted horizontal line from the intersection of the maximum stable bubble diameter and the curve for the particle Reynolds No. of 50 represents the time to the maximum stable bubble diameter at the particle Reynolds No. of 50. The right vertical line in the plot represents the maximum stable bubble diameter at a particle Reynolds No. of 3600, corresponding to the lower curve, for a fuel gas emitted from the jet of gas extending from the nozzle 29 of the fuel distributor 28. The dotted horizontal line from the intersection of the maximum stable bubble diameter and the curve for the particle Reynolds No. of 3600 represents the time to the maximum stable bubble diameter at the particle Reynolds No. of 3600.

The particle Reynolds No. should be calculated according to Equation (1):

$$N_{Re,p} = \frac{(v_f \times D_p \times \rho_f)}{\mu_f} \quad (1)$$

wherein $N_{Re,p}$ is the particle Reynolds No., $v_f$ is the velocity of the fuel gas exiting the discharge nozzle 29 of the fuel distributor, $D_p$ is Sauter mean diameter of the catalyst particles, $\rho_f$ is the density of the fuel gas and $\mu_f$ is the dynamic viscosity of the fuel gas. The $N_{Re,p}$ should be between about 40 and about 4000 and preferably between about 50 and about 3600. If the Reynolds No. is based on the fluid, $N_{Re,f}$, $D_n$ representing the inner diameter of the discharge nozzle 29 of the fuel distributor is substituted for $D_p$ in Equation (1) as shown in Equation (2):

$$N_{Re,f} = \frac{(v_f \times D_n \times \rho_f)}{\mu_f} \quad (2)$$

The $N_{Re,f}$ selected should be between about 10,000 and about 2,000,000.

Time to Bubble Diameter is calculated as the distance the bubble has traveled from the jet divided by the velocity of the bubble of a given diameter pursuant to the V. Bejcek et al., BUBBLE SIZE ABOVE AN ISOLATED GAS JET PENETRATING A FLUIDIZED BED, Chem. Eng. Comm., vol. 62, 303-14 (1987), which is incorporated herein by reference.

The maximum stable bubble size, De max, is calculated from formula (3):

$$D_{e\ max} = 2\left[\frac{U_t^2}{g}\right] \quad (3)$$

wherein, $U_t$ is the terminal velocity of particles calculated for a particle that is 2.7 times the Sauter mean diameter of the particles and g is the gravitational constant. Handbook of Powder Technology, GAS FLUIDIZATION, vol. 8, Mel Pell, Ed. (1990).

Bubbles that have not achieved the maximum stable bubble diameter before the fuel gas induction time will generate a flame whose intense heat can damage equipment and catalyst. In calculations, we utilized an induction time from the GRI-MECH 3.0 Microkinetic Mechanism at http://combustion.berkeley.edu/gri-mech/.

In the example in FIG. 2, the induction time for oxidization of the fuel gas is 1.7 seconds which is significantly greater than maximum time for stable bubble diameter of 0.25 seconds. Bubbles that break up after exceeding the maximum stable bubble diameter will not produce a flame. The resulting smaller bubbles may also grow to the maximum stable bubble diameter before breaking up. A particle Reynolds No. should be selected that produces a bubble that achieves the maximum stable bubble diameter before reaching the induction time to avoid flame generation. A maximum stable bubble diameter should be between about 0.1 and about 0.5 meters, preferably between about 0.15 and 0.45 meters, and a time to maximum stable bubble diameter should be about 0.02 and under an induction time such as about 1.7 s, about 1 s, about 0.8 s or to about 0.40 seconds and preferably about 0.05 and about 0.25 seconds. These regenerator conditions will ensure that fuel gas combusts evenly without causing a flame which can damage the catalyst or equipment.

The rate of fuel gas distributed to the regenerator 10 through fuel distributors 28 may be adjusted to meet a predetermined temperature in the regenerator. Locating the fuel distributors 28 at different locations also allows distribution of fuel gas with varying propensities for combustion based on the contact time, temperature and oxygen concentration at that location. Moreover, fuel injection into various locations can be designed to control or limit the maximum temperature to which catalyst is exposed to preserve catalyst from thermal damage.

Turning back to the mixing chamber 50, the spent catalyst and the regenerated catalyst are separately added to the mixing chamber and mixed before exiting from the mixing chamber. The mixed spent and regenerated catalyst does not have a significant concentration gradient of coke from one area to another, where coke is present on the spent catalyst at about 0.02 to about 2.5 weight percent but the regenerated catalyst has essentially no coke. For mixed catalyst as compared to merely combined catalyst, the total weight percent of coke for any one sample may vary from the average coke concentration by about 10 weight percent or less, or about 5 weight percent less, or about 3 weight percent or less in various embodiments. Therefore, "mixed catalyst" is defined as catalyst with an insignificant concentration gradient of coke, where an insignificant concentration gradient of coke is such that the weight percent of coke on any standard sample size (such as one hundred grams of catalyst) varies from the average coke concentration by about 10 percent or less, 5 percent or less, or 3 percent or less in various embodiments. To illustrate, for a 50/50 mixture of spent and regenerated catalyst with 2.5 grams of coke per 100 grams of spent catalyst, the average coke concentration will be 1.25 grams of coke per 100 grams of sample (½ spent catalyst with 2.5 grams coke per 100 grams of spent catalyst, and ½ regenerated catalyst with 0 grams coke per 100 grams of regenerated catalyst). In an exemplary embodiment with 5 weight percent variation or less, any sample of mixed catalyst will have within 5 weight percent of 1.25 grams of coke per 100 grams of sample, so any 100-gram sample will have from about 1.1875 grams to about 1.3125 grams of coke.

A mixing tube 60 may be positioned within the mixing chamber 50 in an embodiment, to facilitate mixing between the spent catalyst and the regenerated catalyst. The mixing tube 60 and an exterior wall 62 of the mixing chamber 50 may define an annulus 64 therebetween. The spent catalyst pipe inlet 12i and the regenerated catalyst pipe inlet 16i open into the annulus 64 in some embodiments. The regenerated catalyst pipe inlet 16i may be located lower in the mixing chamber 60 than the spent catalyst pipe inlet 12i. The mixing tube 60 may be radially centered within the mixing chamber 50, and the mixing tube 60 may be cylindrical in shape. The mixing tube 60 may have a central longitudinal axis (not illustrated) aligned with a central longitudinal axis (not illustrated) of the mixing chamber 50. A lateral wall 66 of the mixing tube 60 may be vertical in some embodiments. The air distributor 52 may be positioned at least partially within the annulus 64 and/or in the mixing tube 60 in some embodiments.

In an exemplary embodiment, one or more tube openings 68 are defined in the lateral wall 66 of the mixing tube 60. The tube opening 68 serves as an entrance into an interior 70 of the mixing tube 60, and the tube opening can also serve as an exit from the interior 70. In an exemplary embodiment, one or more of the tube openings 68 have an elongated configuration such that an upper edge of the tube opening 68 is spaced from the near a top of the mixing tube 60 such as from 0.2 tube diameters from the top. In alternate embodiments (not illustrated), one or more of the tube openings 68 may include two or more openings, with one opening above the other such that the openings are radially aligned on the mixing tube 60. The spent catalyst and the regenerated catalyst from the spent catalyst pipe inlet 12$i$ and the regenerated catalyst pipe inlet 16$i$, respectively, may enter the interior 70 through the tube opening 68 and then exit the interior 70 through the tube opening 68. This sequence facilitates mixing of the spent catalyst stream and the regenerated catalyst stream in the interior 70 of the mixing tube 60 and in the annulus 64. The mixing in the mixing chamber 60 produces a thoroughly mixed catalyst of sufficient temperature to promote combustion of coke on catalyst and the fuel gas upon contact. The mixing of the spent catalyst and the regenerated catalyst ensures that combustion occurs in the dense catalyst phase, so sufficient heat sink is available to absorb the heat, thus avoiding transferring excessive heat to surrounding equipment and catalyst in the dilute phase potentially damaging it and maximizing the enthalpy transferred back to the endothermic reaction through the medium of the regenerated catalyst.

The interior 70 of the mixing tube 60 is in fluid communication with the annulus 64 through the tube opening 68. In an exemplary embodiment, the upper edge of the tube opening 68 is above the lower edge of the spent catalyst pipe inlet 12$i$ and the regenerated catalyst pipe inlet 16$i$ and is optionally above or at the same elevation as the upper edge of the spent catalyst pipe inlet 12$i$ and the regenerated catalyst pipe inlet 16$i$, as well. The upper edge of the spent catalyst pipe inlet 12$i$ is the highest elevation of the intersection of the spent catalyst standpipe 12 with the mixing chamber 50, the lower edge is the lowest elevation of the intersection of the spent catalyst standpipe 12 with the mixing chamber 50, and the same relationship may apply to other inlets. In embodiments with the upper edge of the tube opening 68 above the upper edge of the spent catalyst pipe inlet 12$i$ and the regenerated catalyst pipe inlet 16$i$, the catalyst from the spent catalyst pipe inlet 12$i$ and the regenerated catalyst pipe inlet 16$i$ can flow upwardly with the fluidizing gas from the mixing gas distributor 52 through the tube opening 68 and into the interior 70 of the mixing tube 60. In this embodiment, the air distributor 52 may be located in part in the interior 70 of the mixing tube 60.

Figure 3:
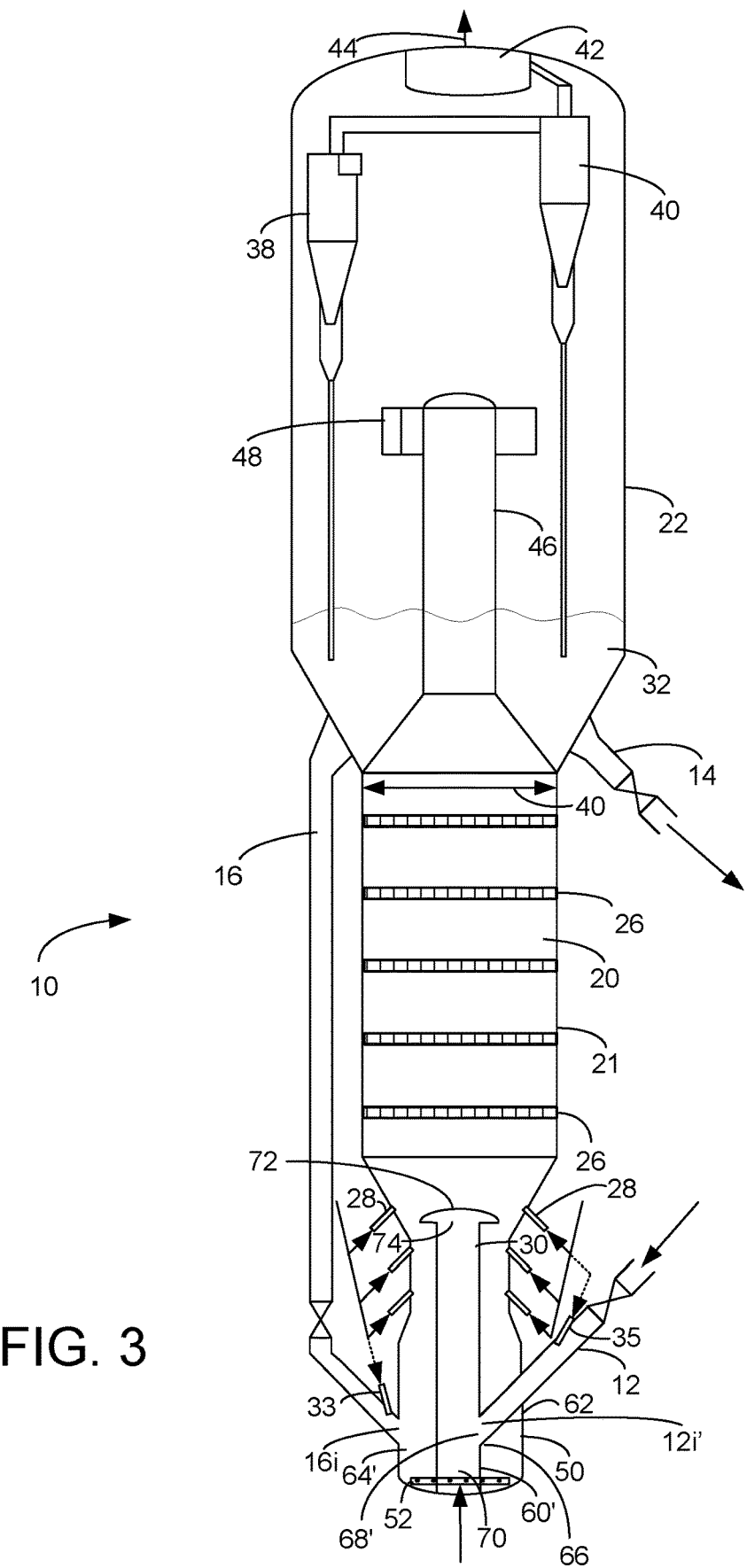
FIG. 3 is a schematic drawing of an alternative embodiment of FIG. 1.

FIG. 3 illustrates an alternative embodiment to FIG. 1 in which the mixing tube 60' extends from the mixing chamber 50' into the fuel distribution section 30', thereby extending the annulus 64' also. Many of the elements in FIG. 3 have the same configuration as in FIG. 1 and bear the same reference number. Elements in FIG. 3 that correspond to elements in FIG. 1 but have a different configuration bear the same reference numeral as in FIG. 1 but are marked with a prime symbol (').

In FIG. 3, an opening 68' in the lateral wall 66' in the mixing tube 60' is coterminous with the regenerated catalyst pipe inlet 12$i$'. It is contemplated that the mixing tube 60' could be coterminous with the spent catalyst pipe inlet 16$i$. However, in the embodiment of FIG. 3, the spent catalyst standpipe 12 feeds the spent catalyst into the mixing tube 60' through the spent catalyst inlet 12$i$' and the spent catalyst ascends up the interior 70 of the mixing tube 60'. Meanwhile regenerated catalyst from the regenerated catalyst pipe inlet 16$i$ ascends up the annulus 64' separate from the spent catalyst. Fluidizing oxygen supply gas is distributed from the oxygen supply gas distributor 52 into the mixing tube 60' and the annulus 64' to lift the respective catalyst in each.

The fuel gas is distributed from the fuel distributors 28 into the annulus carrying the hot regenerated catalyst and instantly combusts further increasing the temperature in the annulus 64'. A baffle 72 is positioned above the mixing tube 60'. The mixing tube 60' has an upper open end 74 that is spaced apart from the baffle 72. The spent catalyst exits the open end 74 and is directed downwardly into the upflowing hot regenerated catalyst and combusting fuel gas in the annulus 64' by the baffle 72. The baffle 72 may have a hemispherical configuration with an apex spaced apart from the upper open end 74. The spent catalyst mixes with the very hot regenerated catalyst due to the fuel gas combustion and is quickly heated. Coke on the spent catalyst instantly begins to combust as the mixture of spent catalyst, regenerated catalyst, air and fuel gas ascend into the combustion vessel 20.

It is also contemplated that fuel gas may be injected into the regenerated catalyst pipe from a fuel distributor 33 with an inlet in the regenerated catalyst pipe 16 perhaps proximate the regenerated catalyst pipe inlet 16$i$ to initiate combustion even earlier in the process. It is further contemplated that fuel gas may be injected into the spent catalyst pipe from a fuel distributor 35 with an inlet in the spent catalyst pipe 12 perhaps proximate the spent catalyst pipe inlet 12$i$ to initiate combustion even earlier in the process but at a lower temperature.

It is also contemplated that the baffle 72 of FIG. 3 could be used above the mixing chamber 50 in the embodiment of FIG. 1 to prevent bypassing before mixing.

By mixing spent catalyst and regenerated catalyst combustion is able to occur in the presence of a dense catalyst phase to ensure sufficient heat sink is available to absorb the heat of combustion without undue temperature rise. Moreover, by mixing spent catalyst and regenerated catalyst before they contact the supplemental fuel gas or by distributing the fuel gas into the regenerated catalyst, the fuel gas begins combustion at a hotter temperature than by initial contact with cooler spent catalyst. The combustion is performed at a hotter temperature and is more likely to completely combust the fuel gas while in contact with the denser catalyst phase all the way to carbon dioxide. Moreover, by selecting appropriate fluidization conditions flames can be suppressed to ensure even combustion and heat release. Consequently, a predominance of the heat is absorbed by the catalyst in the dense catalyst phase to ensure sufficient catalyst absorbs the heat of combustion to prevent excessive temperatures that the catalyst and the equipment cannot withstand without damage and that the heat transfer by catalyst to the endothermic dehydrogenation reaction zone is maximized.

SPECIFIC EMBODIMENTS

While the following is described in conjunction with specific embodiments, it will be understood that this description is intended to illustrate and not limit the scope of the preceding description and the appended claims.

A first embodiment of the disclosure is a catalyst regenerator for a catalytic dehydrogenation process comprising a mixing chamber including a spent catalyst pipe inlet and a regenerated catalyst pipe inlet for mixing spent catalyst and regenerated catalyst together; an oxygen supply gas distributor for distributing an oxygen supply gas to the catalyst; a combustion chamber in which coke is combusted from the spent catalyst in the presence of oxygen; and a fuel distributor for distributing fuel gas to the regenerator for combustion in the combustion chamber. An embodiment of the disclosure is one, any or all of prior embodiments in this paragraph up through the first embodiment in this paragraph further comprising a mixing tube in the mixing chamber to facilitate mixing between the spent catalyst, the regenerated catalyst. An embodiment of the disclosure is one, any or all of prior embodiments in this paragraph up through the first embodiment in this paragraph further comprising an opening in a lateral wall of the tube. An embodiment of the disclosure is one, any or all of prior embodiments in this paragraph up through the first embodiment in this paragraph wherein the opening in the tube is coterminous with one of the spent catalyst pipe inlet and the regenerated catalyst pipe inlet. An embodiment of the disclosure is one, any or all of prior embodiments in this paragraph up through the first embodiment in this paragraph further comprising a fuel distribution section that comprises fuel injectors penetrating through a wall of the regenerator. The catalyst regenerator wherein the fuel distributor is in the regenerated catalyst pipe. An embodiment of the disclosure is one, any or all of prior embodiments in this paragraph up through the first embodiment in this paragraph further including a baffle above the tube.

A second embodiment of the disclosure is a process for regenerating dehydrogenation catalyst from a catalytic dehydrogenation reaction comprising mixing spent catalyst and regenerated catalyst together to provide a mixture of catalyst; distributing an oxygen supply gas to the catalyst; distributing fuel to the catalyst; and combusting the fuel and carbon on the spent catalyst with oxygen supply gas to provide flue gas and regenerated catalyst. An embodiment of the disclosure is one, any or all of prior embodiments in this paragraph up through the second embodiment in this paragraph further comprising separating the flue gas from the regenerated catalyst; recycling a portion of the regenerated catalyst to the mixing step; transporting another portion of the regenerated catalyst to the catalytic dehydrogenation process. An embodiment of the disclosure is one, any or all of prior embodiments in this paragraph up through the second embodiment in this paragraph further comprising combusting carbon on the spent catalyst with oxygen supply gas while the oxygen supply gas and catalyst ascend in a regenerator. An embodiment of the disclosure is one, any or all of prior embodiments in this paragraph up through the second embodiment in this paragraph wherein the catalyst is a dehydrogenation catalyst comprises a small to medium pore molecular sieve or is amorphous and incorporates a dehydrogenation metal. An embodiment of the disclosure is one, any or all of prior embodiments in this paragraph up through the second embodiment in this paragraph wherein a rate of regenerated catalyst to the mixing step is 0.5 to 10 times the rate of spent catalyst to the mixing step. An embodiment of the disclosure is one, any or all of prior embodiments in this paragraph up through the second embodiment in this paragraph wherein one of the spent catalyst and the regenerated catalyst is fed to a tube and the other of the spent catalyst and the regenerated catalyst is fed to an annulus outside of the tube. An embodiment of the disclosure is one, any or all of prior embodiments in this paragraph up through the second embodiment in this paragraph wherein the spent catalyst and the regenerated catalyst are mixed in a mixing chamber and the fuel gas contacts the mixture after the mixture exits the mixing chamber. An embodiment of the disclosure is one, any or all of prior embodiments in this paragraph up through the second embodiment in this paragraph wherein the oxygen supply gas lifts the catalyst in the mixing chamber. An embodiment of the disclosure is one, any or all of prior embodiments in this paragraph up through the second embodiment in this paragraph further comprising distributing fuel gas to the regenerated catalyst before mixing the spent catalyst and the regenerated catalyst.

A third embodiment of the disclosure is an catalyst regenerator for a catalytic dehydrogenation process comprising a mixing chamber including a spent catalyst pipe inlet and a regenerated catalyst pipe inlet for mixing spent catalyst and regenerated catalyst together and an oxygen supply gas distributor for distributing an oxygen supply gas to the catalyst. a combustion chamber in which coke is combusted from the spent catalyst in the presence of oxygen; and a fuel distribution section between the mixing chamber and the combustion chamber including fuel distributors for distributing fuel to the regenerator for combustion in the combustion chamber. An embodiment of the disclosure is one, any or all of prior embodiments in this paragraph up through the third embodiment in this paragraph further comprising a mixing tube in the mixing chamber to facilitate mixing between the spent catalyst, the regenerated catalyst and the oxygen supply gas in an annulus between the mixing tube and a wall of the mixing chamber. An embodiment of the disclosure is one, any or all of prior embodiments in this paragraph up through the third embodiment in this paragraph further comprising an opening in a lateral wall of the tube. An embodiment of the disclosure is one, any or all of prior embodiments in this paragraph up through the third embodiment in this paragraph wherein the fuel distribution section comprises fuel injectors penetrating through a wall of the section.

A fourth embodiment of the disclosure is a process for regenerating spent catalyst from a catalytic reaction comprising distributing an oxygen supply gas to the spent catalyst; distributing a fuel gas to the spent catalyst through a discharge nozzle 29 at a particle Reynolds No. based on the spent catalyst of about 40 to about 4000; and combusting the fuel gas and carbon on the spent catalyst with oxygen from the oxygen supply gas to provide flue gas and regenerated catalyst. An embodiment of the disclosure is one, any or all of prior embodiments in this paragraph up through the fourth embodiment in this paragraph wherein bubbles of the fuel gas break up into smaller bubbles before its induction time. An embodiment of the disclosure is one, any or all of prior embodiments in this paragraph up through the fourth embodiment in this paragraph further comprising a fluid Reynolds No. based on the fuel gas of about 10,000 to about 2,000,000. An embodiment of the disclosure is one, any or all of prior embodiments in this paragraph up through the fourth embodiment in this paragraph further comprising distributing the fuel gas to the spent catalyst with a maximum stable bubble size of between about 0.1 and 0.5 m. An embodiment of the disclosure is one, any or all of prior embodiments in this paragraph up through the fourth embodiment in this paragraph further comprising distributing the fuel gas to the spent catalyst with time to maximum stable bubble size of about 0.05 to about 1.7 seconds.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A catalyst regenerator for a catalytic dehydrogenation process comprising:
   a mixing chamber including a spent catalyst pipe inlet and a regenerated catalyst pipe inlet for mixing spent catalyst and regenerated catalyst together;
   an oxygen supply gas distributor for distributing an oxygen supply gas to the spent catalyst;
   a combustion chamber in which coke is combusted from said spent catalyst in the presence of oxygen; and
   a fuel distributor for distributing fuel gas to the regenerator for combustion in the combustion chamber.

2. The catalyst regenerator of claim 1 further comprising a mixing tube in said mixing chamber to facilitate mixing between said spent catalyst, said regenerated catalyst.

3. The catalyst regenerator of claim 2 further comprising an opening in a lateral wall of said tube.

4. The catalyst regenerator of claim 3 wherein the opening in said tube is coterminous with one of the spent catalyst pipe inlet and the regenerated catalyst pipe inlet.

5. The catalyst regenerator of claim 1 further comprising a fuel distribution section that comprises fuel injectors penetrating through a wall of said regenerator.

6. The catalyst regenerator of claim 1, wherein said fuel distributor is in a regenerated catalyst pipe.

7. The catalyst regenerator of claim 2 further including a baffle above said tube.

8. The process of claim 1 further comprising distributing said fuel gas to said spent catalyst with a maximum stable bubble size of between about 0.1 and about 0.5 m.

9. The process of claim 1 further comprising distributing said fuel gas to said spent catalyst with a time to maximum stable bubble size from 0.05 seconds to about 1.7 seconds.

10. A process for regenerating dehydrogenation catalyst from a catalytic dehydrogenation reaction comprising:
    mixing spent catalyst and regenerated catalyst together to provide a mixture of catalyst;
    distributing an oxygen supply gas to said spent catalyst;
    distributing a fuel gas to said spent catalyst; and
    combusting said fuel gas and carbon on said spent catalyst with oxygen supply gas to provide flue gas and regenerated catalyst.

11. The process of claim 10 further comprising:
    separating said flue gas from said regenerated catalyst;
    recycling a portion of said regenerated catalyst to said mixing step;
    transporting another portion of said regenerated catalyst to the catalytic dehydrogenation process.

12. The process of claim 10 further comprising combusting carbon on said spent catalyst with oxygen supply gas while the oxygen supply gas and catalyst ascend in a regenerator.

13. The process of claim 10 wherein said dehydrogenation catalyst comprises a small to medium pore molecular sieve or is amorphous and incorporates a dehydrogenation metal.

14. The process of claim 10 wherein a rate of regenerated catalyst to said mixing step is 0.5 to 10 times the rate of spent catalyst to the mixing step.

15. The process of claim 10 wherein one of said spent catalyst and said regenerated catalyst is fed to a tube and the other of said spent catalyst and said regenerated catalyst is fed to an annulus outside of said tube.

16. The process of claim 10 wherein said spent catalyst and said regenerated catalyst are mixed in a mixing chamber and said fuel gas contacts said mixture after said mixture exits said mixing chamber.

17. The process of claim 16 wherein said oxygen supply gas lifts said catalyst in said mixing chamber.

18. The process of claim 10 further comprising distributing said fuel gas to said regenerated catalyst before mixing said spent catalyst and said regenerated catalyst.

19. A catalyst regenerator for a catalytic dehydrogenation process comprising:
    a mixing chamber including a spent catalyst pipe inlet and a regenerated catalyst pipe inlet for mixing spent catalyst and regenerated catalyst together and an oxygen supply gas distributor for distributing an oxygen supply gas to the spent catalyst;
    a combustion chamber in which coke is combusted from said spent catalyst in the presence of oxygen; and
    a fuel distribution section between said mixing chamber and said combustion chamber including fuel distributors for distributing fuel to the regenerator for combustion in the combustion chamber.

20. The catalyst regenerator of claim 19 further comprising a mixing tube in said mixing chamber to facilitate mixing between said spent catalyst, said regenerated catalyst and said oxygen supply gas in an annulus between said mixing tube and a wall of the mixing chamber.

21. The catalyst regenerator of claim 19 further comprising an opening in a lateral wall of said tube.

22. The catalyst regenerator of claim 19 wherein said fuel distribution section comprises fuel injectors penetrating through a wall of said section.

23. A process for regenerating spent catalyst from a catalytic reaction comprising:
    distributing an oxygen supply gas to the spent catalyst;
    distributing a fuel gas to said spent catalyst through a discharge nozzle at a particle Reynolds No. based on the spent catalyst of about 40 to about 4000; and
    combusting said fuel gas and carbon on said spent catalyst with oxygen from said oxygen supply gas to provide flue gas and regenerated catalyst.

24. The process of claim 23 wherein bubbles of the fuel gas break up into smaller bubbles before its induction time.

25. The process of claim 23 further comprising a fluid Reynolds No. based on the fuel gas of about 10,000 to about 2,000,000.

* * * * *